United States Patent [19]
Urbahns et al.

[11] Patent Number: 6,147,087
[45] Date of Patent: Nov. 14, 2000

[54] USE OF 1,2-BRIDGED 1,4-DIHYDROPYRIDINES AS MEDICAMENTS

[75] Inventors: Klaus Urbahns, Wuppertal; Hans-Georg Heine, Krefeld; Bodo Junge, Wuppertal; Thomas Glaser, Overath; Reilinde Wittka, Köln; Jean-Marie-Viktor De Vry, Rösrath; Henning Sommermeyer, Köln, all of Germany

[73] Assignee: Bayer Aktiengesellschaft, Leverkusen, Germany

[21] Appl. No.: 09/362,409

[22] Filed: Jul. 28, 1999

Related U.S. Application Data

[62] Division of application No. 08/569,534, Dec. 8, 1995, Pat. No. 5,990,121.

[30] Foreign Application Priority Data

Dec. 16, 1994 [DE] Germany .................. 44 44 860

[51] Int. Cl.$^7$ ..................... A61K 31/44; C07D 221/02
[52] U.S. Cl. ........................... 514/299; 546/112
[58] Field of Search .............. 546/112; 514/299

[56] References Cited

U.S. PATENT DOCUMENTS

| | | | |
|---|---|---|---|
| 3,867,393 | 2/1975 | Meyer et al. | 546/321 |
| 3,935,220 | 1/1976 | Meyer et al. | 546/112 |
| 3,951,988 | 4/1976 | Meyer et al. | 540/503 |
| 4,053,614 | 10/1977 | Meyer et al. | 546/112 |
| 5,225,566 | 7/1993 | Butera et al. | 548/361.5 |

FOREIGN PATENT DOCUMENTS 2210633  9/1973  Germany .

OTHER PUBLICATIONS

Porsolt, R.D. et al., "Behavioral Despair in Rats: A New Model Sensitive to Antidepressant Treatments," Eur.J.Pharmacol. 1978, vol. 47, No. 4, pp. 379–391, abstract only.

Etcheberrigaray, E. et al., Annals of the New York Acad.Sci. Dec. 15, 1994, vol. 747, pp. 245–55, online search results relied upon.

Heinemann, U. et al.,Epilepsy Res. Suppl. 1992, vol. 9, pp. 107–14, online search results relied upon.

Lee, Y.S. et al, Cellular Signalling, Nov. 1993, 5(6), pp. 803–9, online search results relied upon.

Shang, H. et al., Pharm.Toxicol.Dec. 1994, vol. 75(6), pp. 327–36, online search results relied upon.

Furspan, P.B. et al., Hypertension, Feb. 1990, 15(suppl.2), pp. 197–1101.

H.Meyer, et al., Liebegs Ann.Chem., pp.1888–1894 (1977).

P.W.L. Tas, et al., Neuroscience Letters, vol. 94, pp.279–284 (1988).

Pflugers Archiv.European Journal Of Physiology, vol. 429, No. 2, Dec. 1994, pp.176–182.

J.C. Ellory, et al., Br.J. Pharmacol. vol. 111, pp.903–905 (1994).

*Primary Examiner*—Zinna Northington Davis
*Attorney, Agent, or Firm*—Norris, McLaughlin & Marcus, P.A.

[57] ABSTRACT

The present invention relates to the new use of 1,2-bridged 1,4-dihydropyridines which are known in some cases, of the general formula (I)

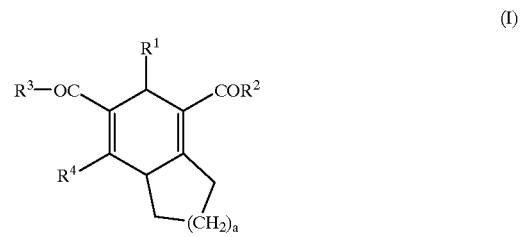

in which $R^1$ to $R^4$ and a have the meaning indicated in the description, processes for their preparation and their use as medicaments, as selective potassium channel modulators, in particular for the treatment of the central nervous system.

3 Claims, No Drawings

USE OF 1,2-BRIDGED 1,4-DIHYDROPYRIDINES AS MEDICAMENTS

This application is a divisional of application Ser. No. 08/569,534, filed on Dec. 8, 1995 (now U.S. Pat. No. 5,990,121).

The present invention relates to the new use of 1,2-bridged 1,4-dihydropyridines which are known in some cases, processes for their preparation and their use as medicaments, as selective potassium channel modulators, in particular for the treatment of the central nervous system.

1,2-Bridged 1,4-dihydropyridine-3,5-dicarboxylic acid esters are known from the publication Justus Liebigs Ann. Chem. (1977), 11–12, 1888–94.

1,2-Hexa- and 1,2-pentamethylene-1,4-dihydropyridine derivatives having circulatory action are additionally described [cf. US 39 519 88; US 39 35 220 and DE 22 10 633].

It has been found that the 1,2-bridged 1,4-dihydropyridines which are known in some cases, of the general formula (I)

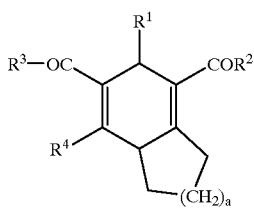

(I)

in which
$R^1$ represents aryl having 6 to 10 carbon atoms, which is optionally substituted up to 5 times by identical or different nitro, cyano, halogen or trifluoromethyl substituents or by straight-chain or branched alkylthio having up to 6 carbon atoms,
$R^2$ and $R^3$ are identical or different and each represent straight-chain or branched alkyl or alkoxy having up to 8 carbon atoms or phenyl,
a represents a number 1, 2 or 3,
$R^4$ represents methyl, or
$R^3$ and $R^4$ together form a radical of the formula —$CH_2$—$CH_2$—$CH_2$— or —$CH_2$—$C(CH_3)_2$—$CH_2$—,
surprisingly have a selective modulating action on potassium channels and are suitable for use in the control of disorders of the central nervous system and sickle cell anemia.

The compounds according to the invention can exist in stereoisomeric forms which behave either as image and mirror image (enantiomers), or which do not behave as image and mirror image (diastereomers). The invention relates both to the antipodes and to the racemic forms as well as the diastereomer mixtures. Like the diastereomers, the racemic forms can also be separated into the stereoisomerically uniform constituents in a known manner.

Preferably used compounds of the general formula (I) are those in which
$R^1$ represents phenyl or naphthyl, each of which is optionally substituted up to 3 times by identical or different nitro, cyano, fluorine, chlorine, bromine, iodine or trifluoromethyl substituents or by straight-chain or branched alkylthio having up to 4 carbon atoms,
$R^2$ and $R^3$ are identical or different and each represent straight-chain or branched alkyl or alkoxy having up to 4 carbon atoms or phenyl,
a represents a number 1 or 2,
$R^4$ represents methyl, or
$R^3$ and $R^4$ together form a radical of the formula —$CH_2$—$CH_2$—$CH_2$— or —$CH_2$—$C(CH_3)_2$—$CH_2$—,
in the control of disorders of the central nervous system.

Particularly preferably used compounds of the general formula (I) are those in which
$R^1$ represents phenyl which is optionally substituted up to 2 times by identical or different nitro, cyano, fluorine, chlorine, bromine, iodine, trifluoromethyl substituents or by methylthio,
$R^2$ and $R^3$ are identical or different and each represent methyl, ethyl or methoxy,
a represents a number 1 or 2,
$R^4$ represents methyl, or
$R^3$ and $R^4$ together form a radical of the formula —$CH_2$—$CH_2$—$CH_2$— or —$CH_2$—$C(CH_3)_2$—$CH_2$—,
in the control of disorders of the central nervous system.

The compounds of the general formula (I) according to the invention show an unforeseeable, useful spectrum of pharmacological action.

They are channel modulators having a surprising selectivity for calcium-dependent potassium channels of high conductivity (BK(Ca) channels), in particular the potassium channels of the central nervous system.

On account of their pharmacological properties, they can be employed for the production of medicaments for the treatment of degenerative central nervous system disorders, such as e.g. on occurrence of dementias (multiinfarct dementia (MID), primary degenerative dementia (PDD), pre- and senile Alzheimer's disease, HIV dementia and other forms of dementia), Parkinson's disease or amyotropic lateral sclerosis and multiple sclerosis.

The active compounds are furthermore suitable for the treatment of brain function disorders in old age, of organic brain syndrome (OBS) and of age-related memory disorders (age-associated memory impairment (AAMI).

They are suitable for the prophylaxis, treatment and for the control of the sequelae of cerebral circulatory disorders such as cerebral ischaemias, strokes, craniocerebral traumata and of subarachnoid haemorrhages.

They useful for the treatment of depressions and psychoses, e.g. schizophrenia. They are additionally suitable for the treatment of disorders of neuroendocrine secretion and of neurotransmitter secretion and health disorders associated therewith such as mania, alcoholism, drug abuse, dependence or abnormal eating behaviour. Further application areas are the treatment of migraine, sleep disorders and of neuropathies. They are moreover suitable as analgesics.

The active compounds are furthermore suitable for the treatment of disorders of the immune system, in particular of T-lymphocytes proliferation and for affecting the smooth musculature, in particular of uterus, urinary bladder and bronchial tracts, and for the treatment of diseases associated therewith such as e.g. asthma and urinary incontinence and for the treatment of arrhythmia, angina and diabetes.

The invention additionally relates to new selected compounds of the general formula (I) and their salts, having the substituent meanings indicated in the following table:

| $R^1$ | $R^2$ | a | $R^3$ | $R^3 + R^4$ | $R^4$ |
|---|---|---|---|---|---|
| m—$NO_2$—$C_6H_4$ | $CH_3$ | 2 | — | —$CH_2$—$CH_2$—$CH_2$— | — |
| p—Cl—$C_6H_4$ | $CH_3$ | 2 | — | —$CH_2$—$CH_2$—$CH_2$— | — |
| o,m—Cl—$C_6H_3$ | $CH_3$ | 2 | — | —$CH_2$—$CH_2$—$CH_2$— | — |
| p—Cl—$C_6H_4$ | $CH_3$ | 1 | — | —$CH_2$—$CH_2$—$CH_2$— | — |
| o,m—Cl—$C_6H_3$ | $CH_3$ | 1 | — | —$CH_2$—$CH_2$—$CH_2$— | — |
| p—Cl—$C_6H_4$ | $CH_3$ | 1 | — | —$CH_2$—$C(CH_3)_2$—$CH_2$— | — |
| o,m—Cl—$C_6H_3$ | $CH_3$ | 1 | — | —$CH_2$—$C(CH_3)_2$—$CH_2$— | — |
| m—$NO_2$—$C_6H_4$ | $CH_3$ | 1 | — | —$CH_2$—$C(CH_3)_2$—$CH_2$— | — |
| o,m—Cl—$C_6H_3$ | $OCH_3$ | 1 | —$CH_3$ | — | $CH_3$ |
| p—Cl—$C_6H_4$ | $OCH_3$ | 1 | —$CH_3$ | — | $CH_3$ |
| p—$NO_2$—$C_6H_4$ | $CH_3$ | 1 | $CH_3$ | — | $CH_3$ |
| m,p—Cl—$C_6H_3$ | $CH_3$ | 1 | $CH_3$ | — | $CH_3$ |
| o,m—Cl—$C_6H_3$ | $CH_3$ | 1 | $CH_3$ | — | $CH_3$ |
| p—$CF_3$—$C_6H_4$ | $CH_3$ | 1 | $CH_3$ | — | $CH_3$ |
| m—$CF_3$, p—Cl—$C_6H_3$ | $CH_3$ | 1 | $CH_3$ | — | $CH_3$ |
| o,m—Cl—$C_6H_3$ | $OCH_3$ | 1 | $OCH_3$ | — | $CH_3$ |
| p—$CF_3$—$C_6H_4$ | $OCH_3$ | 1 | $OCH_3$ | — | $CH_3$ |
| p—Cl—$C_6H_4$ | $OCH_3$ | 2 | $OCH_3$ | — | $CH_3$ |
| p—Cl—$C_6H_4$ | $OCH_3$ | 1 | $OCH_3$ | — | $CH_3$ |

The new and known compounds of the formula (I) according to the invention can be prepared by A) in the case in which $R^3$ and $R^4$ each represent an open-chain radical, converting aldehydes of the general formula (II)

$$R^1\text{—CHO} \quad \text{(II)}$$

in which $R^1$ has the meaning indicated above, first by reaction with dioxo compounds of the general formula (III)

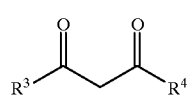

(III)

in which $R^3$ and $R^4$ have the meaning indicated above, in inert solvents, if appropriate in the presence of a base, into the benzylidene compounds of the general formula (IV)

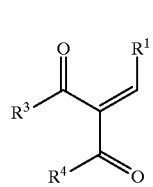

(IV)

in which $R^1$, $R^3$ and $R^4$ have the meaning indicated above, which are optionally isolated, and in a second step reacting with amines of the general formula (V)

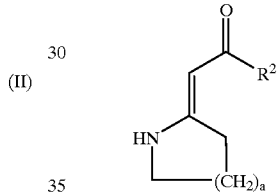

(V)

in which $R^2$ and a have the meaning indicated above, in inert solvents, or (B) in the case in which $R^3$ and $R^4$ together form one of the abovementioned rings, reacting the aldehydes of the general formula (II) with compounds of the general formula (VI)

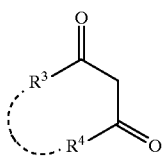

(VI)

in which $R^3$ and $R^4$ together represent a radical of the formula —$CH_2$—$CH_2$—$CH_2$— or —$CH_2$—$C(CH_3)_2$—$CH_2$—, and the cyclic amines of the general formula (V), in a solvent, if appropriate in the presence of a base.

The processes according to the invention can be illustrated by way of example by the following reaction scheme:

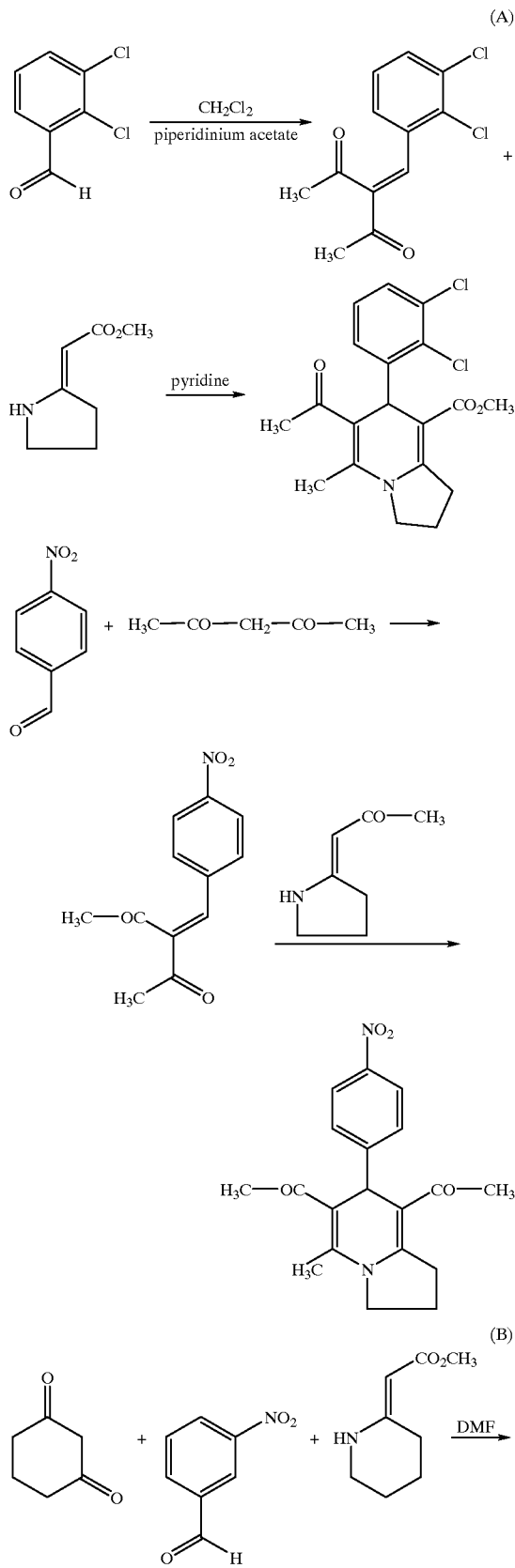

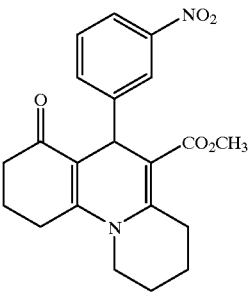

In general, for the first and second step of the process, suitable solvents for process (A) are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, acetone or amides such as hexamethylphosphoramide or dimethylformamide, or halogenated hydrocarbons such as methylene chloride, carbon tetrachloride or hydrocarbons such as benzene or toluene, pyridine or acetic acid. Methylene chloride is preferred for the first step and pyridine or DMF for the second step.

Suitable bases for the first step are in general alkali metal carbonates or alkoxides, such as, for example, potassium carbonate or potassium tert-butoxide, or cyclic amines, such as, for example, piperidine or dimethylaminopyridine or pyridine, or $C_1$–$C_4$-alkylamines, such as, for example, triethylamine.

When carrying out the process according to the invention, any desired ratio of the substances participating in the reaction can be used. In general, however, the reaction is carried out with molar amounts of the reactants.

The reaction temperatures can be varied within a relatively wide range. In general, the reaction is carried out between +10° C. and +200° C., preferably between +20° C. and +100° C., in particular at the boiling point of the respective solvent.

The reactions can be carried out at normal pressure, but also at elevated or reduced pressure (e.g. 0.5 to 3 bar). In general the reaction is carried out at normal pressure.

Suitable solvents for process (B) are also the abovementioned solvents. Dimethylformamide or pyridine is preferred.

The reaction temperatures can be varied within a relatively wide range. In general, the reaction is carried out between +10° C. and +200° C., preferably between +20° C. and +150° C., in particular at the boiling point of the respective solvent.

Enantiomerically pure forms are obtained e.g. by separating diastereomer mixtures of the compounds of the general formula (I), in which $R^2$ or $R^3$ represents an optically active ester radical, according to a customary method, then either directly transesterifying or first preparing the chiral carboxylic acids and then preparing the enantiomerically pure dihydropyridines by esterification.

In general, the diastereomers are separated either by fractional crystallization, by column chromatography or by countercurrent distribution. Which is the optimum process must be decided from case to case, sometimes it is also expedient to use combinations of the individual processes. Separation by crystallization or countercurrent distribution or a combination of both process is particularly suitable.

The enantiomerically pure compounds are also accessible by chromatography of the racemic esters on chiral phases.

The compounds of the general formulae (II), (III), (IV), (V) and (VI) are known per se or can be prepared by customary methods.

The compounds of the general formula (I) according to the invention show an unforeseeable spectrum of action, in particular based on their selectivity for calcium-dependent potassium channels of high conductivity.

[86]Rubidium Efflux from C6-BU1 Glioma Cells

The experiments were carried out with slight modifications according to the method described by Tas et al. (Neurosci. Lett. 94, 279–284, (1988)). To do this rat C6-BU1 glioma cells are used. From the data obtained by liquid scintillation, the increase in the efflux above the basal efflux produced by ionomycin is calculated and set as 100%. The stimulations in the presence of test substances are then related to this value.

The present invention also includes pharmaceutical preparations which, in addition to inert, non-toxic, pharmaceutically suitable auxiliaries and incipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the auxiliary(ies) or excipient(s).

In general, it has proven advantageous to administer the active compound(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, if appropriate it may be advantageous to depart from the amounts mentioned, namely depending on the type and on the body weight of the subject treated, on individual behaviour towards the medicament, the nature and severity of the disorder, the type of preparation and administration, and the time or interval at which administration takes place.

STARTING COMPOUNDS

Example A

Methyl 2-acetyl-3-(2,3-dichlorophenyl)-acrylate

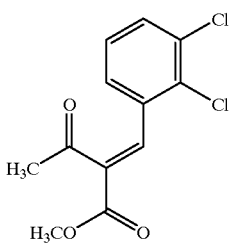

17.5 g (100 mmol) of 2,3-dichlorobenzaldehyde and 11.6 g (100 mmol) of methyl acetoacetate are boiled in a water separator for 3 h with 1 ml of piperidine and 0.5 ml of HOAc in 350 ml of $CH_2Cl_2$. The mixture is then washed twice with water, dried over $MgSO_4$ and concentrated. The residue crystallizes from petroleum ether/ether. Yield: 15.0 g (55%)

Example B 3-(4-Nitrobenzylidene)-pentane-2,4-dione

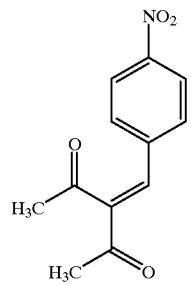

30.2 g (0.2 mol) of 4-nitrobenzaldehyde and 30.0 g (0.3 mol) of acetylacetone are dissolved in 200 ml of isopropanol and treated with 1.2 ml of piperidine and 1 ml of glacial acetic acid. The mixture is warmed in a water bath until a clear solution is formed and then stirred at RT for 4 h. The product precipitates and is filtered off with suction.

After washing with isopropanol and ether, 39.3 g (84%) of the title compound are obtained.

PREPARATION EXAMPLES

Example 1

Dimethyl-(2,3-dichlorophenyl)-5-methyl-1,2,3,7-tetrahydroindolizine-6,8-dicarboxylate

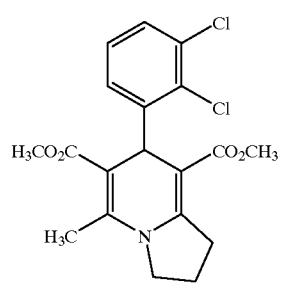

2.7 g (10 mmol) of methyl 2-acetyl-3-(2,3-dichlorophenyl)-acrylate and 1.4 g (10 mmol) of methyl pyrrolidin-2-ylidene-acetate are heated to reflux in 50 ml of isopropanol for 12 h. The reaction mixture is then cooled to RT and treated with 20 ml of petroleum ether. The precipitate which is deposited is filtered off with suction and recrystallized from isopropanol. 1.5 g (37%) of the title compound are obtained.

MS: 395

$R_f$=0.33 (PE/AcOEt=1:1)

m.p.: 173° C.

The compounds listed in Table 1 are prepared in analogy to the procedure of Example 1, optionally if a=2 using methyl piperidin-2-ylidene-acetate.

TABLE 1

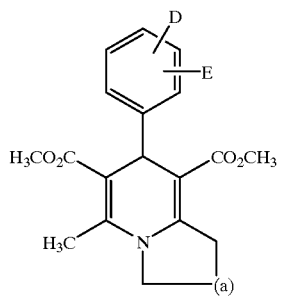

| Ex. No. | D/E | a | Yield (% of theory) | MS | m.p. (0° C.) |
|---|---|---|---|---|---|
| 2 | 4-CF$_3$/H | 1 | 15 | 395 | 129 |
| 3 | 4-Cl/H | 1 | 47 | 361 | 155 |
| 4 | 4-Cl/H | 2 | 51 | 375 | 135 |

Example 5

1-[6-Acetyl-5-methyl-7-(4-nitrophenyl)-1,2,3,7-tetrahydroindolizin-8-yl]ethanone

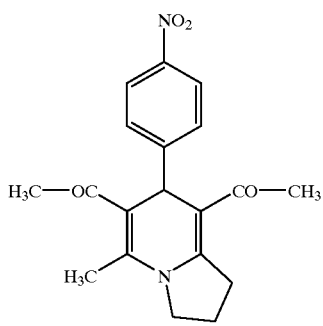

4.66 g (20 mmol) of the compound from Example B and 2.50 g (20 mmol) of 1-pyrrolidin-2-ylidene-propan-2-one are stirred at 100° C. for 20 h in 80 ml of pyridine. The mixture is then concentrated and purified by chromatography (CH$_2$Cl$_2$/AcOEt=10+1). 4.6 g (75%) of the title compound crystallize from AcOEt.

MS: 340

R$_f$=0.16 (PE/AcOEt=1+1)

The compounds listed in Table 2 are prepared in analogy to the procedure of Example 5:

TABLE 2

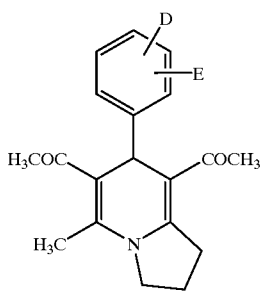

| Ex. No. | D/E | Yield (% of theory) | MS | R$_f$* |
|---|---|---|---|---|
| 6 | 3,4-Cl | 42 | 363 | 0.27 |
| 7 | 2,3-Cl | 72 | 363 | 0.21 |
| 8 | 4-CF$_3$ | 26 | 363 | 0.26 |
| 9 | 4-Cl, 3-CF$_3$ | 61 | 397 | 0.22 |

*PE/AcOEt = 1:1

Example 10

Methyl 6-(3-nitrophenyl)-7-oxo-1,2,3,4,6,7,8,9,10-nonahydropyrido[1,2-a]quinoline-5-carboxylate

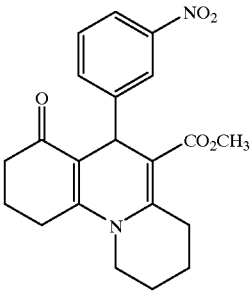

4.28 g (28.3 mmol) of 3-nitrobenzaldehyde, 3.17 g (28.3 mmol) of cyclohexane-1,3-dione and 4.5 g (28.3 mmol) of methyl piperidin-2-ylidene-acetate are kept at reflux in 80 ml of DMF. After 4 h, the mixture is concentrated and the residue is codistilled twice with toluene and purified on silica gel (petroleum ether/CH$_2$Cl$_2$=2:1). The appropriate fractions are concentrated and crystallized from ether. 2.1 g of the title compound are obtained.

MS: 382

R$_f$=0.23

The compounds listed in Table 3 are prepared in analogy to the procedure of Example 10, if a=1 optionally using methyl pyrrolidine-2-acetate:

TABLE 3

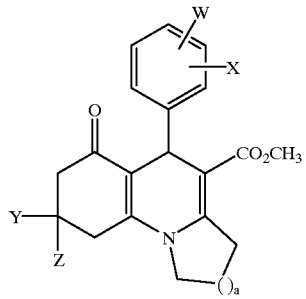

| Ex. No. | W/X | Y | Z | a | $R_f$* | Yield (% of theory) | MS |
|---|---|---|---|---|---|---|---|
| 11 | 3-H, 4-Cl | H | H | 2 | 0.30 | 17 | 371 |
| 12 | 2-Cl, 3-Cl | H | H | 2 | 0.34 | 19 | 405 |
| 13 | 3-H, 4-Cl | H | H | 1 | 0.18 | 55 | 357 |
| 14 | 2-Cl, 3-Cl | H | H | 1 | 0.19 | 25 | 391 |
| 15 | 3-H, 4-Cl | $CH_3$ | $CH_3$ | 1 | 0.38 | 79 | 385 |
| 16 | 2-Cl, 3-Cl | $CH_3$ | $CH_3$ | 1 | 0.39 | 79 | 419 |
| 17 | 2-H, 3-$NO_2$ | H | H | 1 | 0.17 | 35 | 368 |

* = PE/AcOEt 1:1

Example 18

Methyl 6-acetyl-7-(2,3-dichlorophenyl)-5-methyl-1,2,3,7-tetrahydroindolizine-8-carboxylate

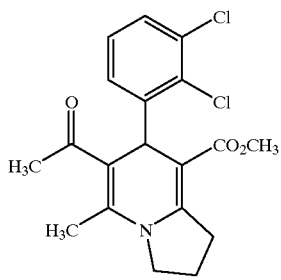

2.57 g (10 mmol) of the compound from Example A are dissolved in pyridine with 1.4 g (10 mmol) of methyl pyrrolidin-2-ylidene-acetate and the mixture is kept at 100° C. for 12 h. The reaction solution is cooled and codistilled twice with toluene and the residue is purified by flash chromatography (petroleum ether/AcOEt=8:1). The title compound crystallizes from $Et_2O$. A yield of 250 mg is obtained (7%).

$R_f$=0.50 (PE/AcOEt=1:1)

MS: 379

The compound listed in Table 4 is prepared in analogy to the procedure of Example 18:

TABLE 4

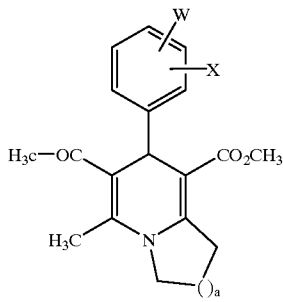

| Ex. No. | W/X | a | MS | Yield (% of theory) | $R_f$* |
|---|---|---|---|---|---|
| 19 | 3-H, 4-Cl | 1 | 345 | 35 | 0.46 |

* = PE/AcOEt = 1:1

What is claimed is:

1. A 1,2-bridged 1,4-dihydropyridine of the formula

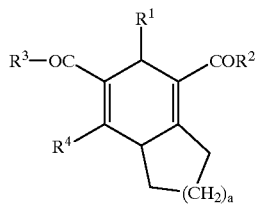

(I)

in which

| $R^1$ | $R^2$ | a | $R^3$ | $R^4$ |
|---|---|---|---|---|
| o,m—Cl—$C_6H_3$ | $OCH_3$ | 1 | —$CH_3$ | — $CH_3$ |
| p—Cl—$C_6H_4$ | $OCH_3$ | 1 | —$CH_3$ | — $CH_3$ |
| p—$NO_2$—$C_6H_4$ | $CH_3$ | 1 | $CH_3$ | — $CH_3$ |
| m,p—Cl—$C_6H_3$ | $CH_3$ | 1 | $CH_3$ | — $CH_3$ |
| o,m—Cl—$C_6H_3$ | $CH_3$ | 1 | $CH_3$ | — $CH_3$ |
| p—$CF_3$—$C_6H_4$ | $CH_3$ | 1 | $CH_3$ | — $CH_3$ |
| m—$CF_3$, p—Cl—$C_6H_3$ | $CH_3$ | 1 | $CH_3$ | — $CH_3$ |
| o,m—Cl—$C_6H_3$ | $OCH_3$ | 1 | $OCH_3$ | — $CH_3$ |
| p—$CF_3$—$C_6H_4$ | $OCH_3$ | 1 | $OCH_3$ | — $CH_3$ |
| p—Cl—$C_6H_4$ | $OCH_3$ | 2 | $OCH_3$ | — $CH_3$ |
| p—Cl—$C_6H_4$ | $OCH_3$ | 1 | $OCH_3$ | — $CH_3$ |

2. A pharmaceutical composition which comprises a pharmaceutically effective amount of a compound according to claim 1 and an inert auxiliary or incipient.

3. A method of treating disorders of the central nervous system in a patient by selective modulating action on potassium channels, said method comprising administering to said patient an effective amount therefore of a compound according to claim 1.

* * * * *